| United States Patent [19] | [11] | 4,296,030 |
|---|---|---|
| Lang, Jr. et al. | [45] | Oct. 20, 1981 |

[54] METAL CHELATES OF 1,4-BIS(SUBSTITUTED-AMINO-5,8-DIHYDROXY-ANTHRAQUINONES

[75] Inventors: Stanley A. Lang, Jr., Stony Point; Keith C. Murdock, Pearl River, both of N.Y.

[73] Assignee: American Cyanamid Company, Stamford, Conn.

[21] Appl. No.: 138,620

[22] Filed: Apr. 9, 1980

[51] Int. Cl.³ .................. C07F 3/06; C07F 15/02; C07F 15/06
[52] U.S. Cl. .................. 260/239 A; 260/366; 260/380; 260/239 E; 260/316; 260/322; 260/239 B; 260/429 R; 544/64; 544/4; 544/225; 544/226; 546/4; 546/11; 546/6; 424/330; 424/246
[58] Field of Search .................. 260/366, 380, 239 E, 260/239 A, 239 AR, 316, 322, 239 B, 429; 544/64, 4, 225, 226; 546/4, 11, 6; 424/246, 330

[56] References Cited

U.S. PATENT DOCUMENTS

| 2,301,286 | 11/1942 | Kern et al. | 260/316 |
| 2,626,255 | 1/1953 | Blumenthal | 546/6 |
| 4,141,992 | 2/1979 | Lang et al. | 260/239 A |

FOREIGN PATENT DOCUMENTS

| 736976 | 6/1966 | Canada | 260/366 |

*Primary Examiner*—Winston A. Douglas
*Assistant Examiner*—Raymond K. Covington
*Attorney, Agent, or Firm*—Edward A. Conroy, Jr.

[57] ABSTRACT

This disclosure describes metal chelates of symmetrical 1,4-bis(substituted-amino)-5,8-dihydroxy-anthraquinones useful for inhibiting the growth of tumors and as colorants or dyes.

9 Claims, No Drawings

METAL CHELATES OF 1,4-BIS(SUBSTITUTED-AMINO-5,8-DIHYDROXY-ANTHRAQUINONES

SUMMARY OF THE INVENTION

This invention relates to metal chelates of new organic compounds and, more particularly, is concerned with metal chelates of symmetrical 1,4-bis(substituted-amino)-5,8-dihydroxyanthraquinones which are represented by the following general formula:

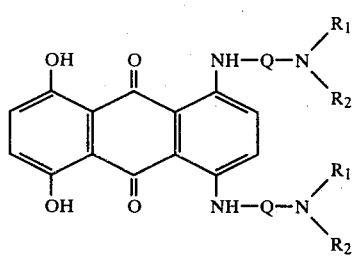

wherein Q is a divalent moiety selected from the group consisting of those of the formulae:

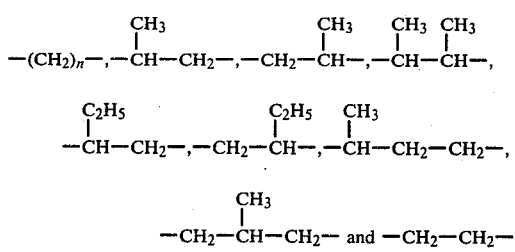

wherein n is an integer from 2 to 4 inclusive; $R_1$ and $R_2$ are each individually selected from the group consisting of hydrogen, alkyl having from 1 to 4 carbon atoms, monohydroxyalkyl having from 2 to 4 carbon atoms with the proviso that the carbon atom alpha to the nitrogen atom does not bear an hydroxy group, dihydroxyalkyl having from 3 to 6 carbon atoms, with the proviso that the carbon atom alpha to the nitrogen atom does not bear an hydroxy group, formyl, alkanoyl having from 2 to 4 carbon atoms, trifluoroacetyl and moieties of the formulae:

—$(CH_2)_n$—CN, —$(CH_2)_n$N—O—R  or

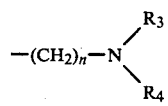

wherein n is an integer from 2 to 4, inclusive, R is alkyl having from 1 to 4 carbon atoms, and $R_3$ and $R_4$ are each individually selected from the group consisting of hydrogen, alkyl having from 1 to 4 carbon atoms, and monohydroxyalkyl having from 2 to 4 carbon atoms, with the proviso that the carbon atom alpha to the nitrogen atom does not bear an hydroxy group; and $R_3$ and $R_4$ taken together with their associated nitrogen atom is morpholino, thiomorpholino, piperazino, 4-methyl-1-piperazino or a moiety of the formula:

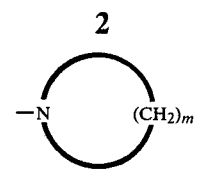

wherein m is an integer from 2 to 6, inclusive; with the proviso that the ratio of the total number of carbon atoms to the sum of the total number of oxygen atoms plus the total number of nitrogen atoms in the side chains at the 1-position and the 4-position does not exceed 4 and with the further proviso that $R_1$ and $R_2$ are not both hydrogen or alkyl. Suitable monohydroxyalkyl and dihydroxyalkyl groups contemplated by the present invention are, for example, β-hydroxyethyl, β-hydroxypropyl, γ-hydroxypropyl, 2,3-dihydroxypropyl, 2,4-dihydroxybutyl, and the like. Also included within the purview of the present invention are the leuco bases and the tautomers thereof which are represented by the following:

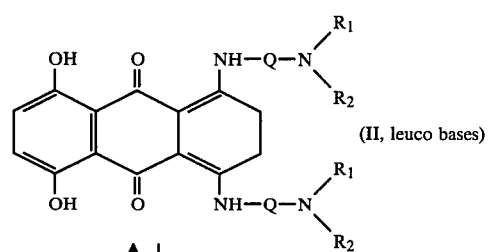

(II, leuco bases)

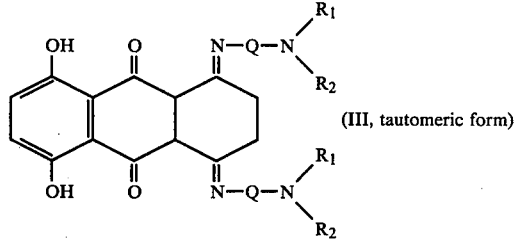

(III, tautomeric form)

wherein $R_1$, $R_2$ and Q are as hereinabove defined.

These compounds form chelates with metal atoms such as platinum, copper, iron, zirconium, cobalt, chromium, zinc and the like, which have an altered active dosage range as compared to the unchelated derivatives and are the essence of this invention.

DETAILED DESCRIPTION OF THE INVENTION

The novel compounds of the present invention are prepared in accordance with the following reaction scheme:

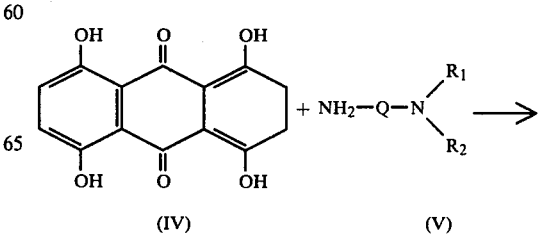

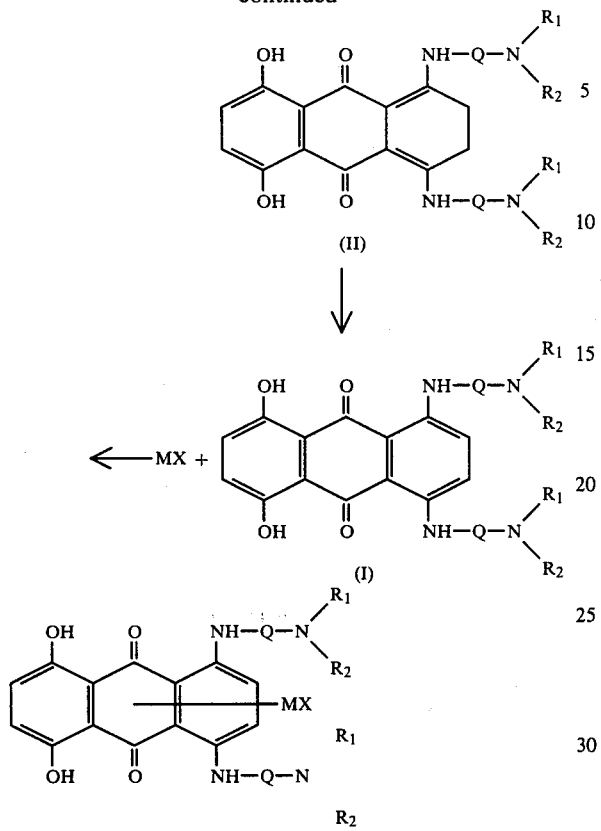

wherein $R_1$, $R_2$ and Q are as hereinabove defined, M is a chelating metal such as iron, platinum, copper, zinc, chromium, zirconium, cobalt or palladium and X is the corresponding counter ion such as halogen, sulfate, nitrate or amine ligand.

In accordance with this reaction scheme, leuco 1,4,5,8-tetrahydroxyanthraquinone (IV) is condensed with an appropriate alkylene diamine (V) in a solvent such as N,N,N',N'-tetramethylethylenediamine, methanol, ethanol, water, dimethylformamide, or mixtures thereof at from about 40° C. to about 60° C. under an atmosphere of nitrogen for several hours to produce the corresponding leuco bases (II). These leuco bases (II) may be readily oxidized to the fully aromatic derivatives (I) by a variety of methods such as air oxidation or treatment with hot nitrobenzene, or treatment with chloranil, hydrogen peroxide, or sodium perborate. The diaminodihydroxyanthraquinone free bases or acid addition salts and the metal salts are heated typically at reflux in a suitable solvent such as water, alcohols, e.g., methanol ethanol, etc. dioxane or mixtures thereof for 1–6 hours. The products are separated by conventional techniques such as by cooling and collecting the precipitate, by cooling and concentrating the solution to give the precipitate, or by removing the solvents to give the product as a residue. The free bases are generated in situ by addition of an alkali metal hydroxide, such as potassium hydroxide or sodium hydroxide, to the solvent.

The novel chelated compounds of the present invention possess the property of inhibiting the growth of transplanted mouse tumors as established by the following tests.

Lymphocytic leukemia P388 test

The animals used are BDF/1 mice all of one sex, weighing a minimum of 18 g. and all within a 3 gram weight range. There are 5 or 6 animals per test group. The tumor transplant is by intraperitoneal injection of 0.5 ml. of dilute ascitic fluid containing $10^6$ cells of lymphocytic leukemia P388. The test compounds are administered intraperitoneally on days one, five and nine (relative to tumor inoculation) at various doses. The animals are weighed and survivors are recorded on a regular basis for 30 days. The median survival time and the ratio of survival time for treated (T)/control (C) animals are calculated. The positive control compound is 5-fluorouracil given as a 60-mg./kg. injection. The results of this test with representative compounds of the present invention appear in Table I. The criterion for efficacy is $T/C \times 100 \geqq 125\%$.

TABLE I

| Lymphocytic Leukemia P388 Test | | | |
|---|---|---|---|
| Compound | Dose (mg./kg.) | Median Survival (Days) | T/C × 100 (percent) |
| 1,4-Bis [2-(2-hydroxyethylamino)ethylamino]-5,8-dihydroxyanthraquinone, dichloride, bis(platinum chloride chelate) | 25 | 30.0 | 300 |
| | 12.5 | 24.0 | 240 |
| | 6.25 | 26.5 | 265 |
| | 3.12 | 21.5 | 215 |
| | 1.56 | 21.0 | 210 |
| Control | 0 | 10.0 | — |
| 5-Fluorouracil | 60 | 21.0 | 210 |
| 1,4-Bis [2-(2-hydroxyethylamino)ethylamino]-5,8-dihydroxyanthraquinone, dichloride, bis(cupric chloride chelate) | 12.5 | 28.0 | 280 |
| | 6.25 | 19.0 | 190 |
| | 3.12 | 19.5 | 195 |
| | 1.56 | 21.5 | 215 |
| Control | 0 | 10.0 | — |
| 5-Fluorouracil | 60 | 21.0 | 210 |
| 1,4-Bis[2-(2-hydroxyethylamino)ethylamino]-5,8-dihydroxyanthraquinone, dichloride, bis(ferrous chloride chelate) | 25 | 30.0 | 300 |
| | 12.5 | 25.5 | 255 |
| | 6.25 | 27.0 | 270 |
| | 3.12 | 24.0 | 240 |
| | 1.56 | 20.5 | 205 |
| Control | 0 | 10.0 | — |
| 5-Fluorouracil | 60 | 21.0 | 210 |
| 1,4-Bis[2-(2-hydroxyethylamino)ethylamino]-5,8-dihydroxyanthraquinone, tetrachloride, bis(dicyclopentadienyl zirconium chelate) | 12.5 | 18.5 | 206 |
| | 6.25 | 30.0 | 333 |
| | 3.12 | 30.0 | 333 |
| | 1.56 | 25.0 | 278 |
| Control | 0 | 9.0 | — |

TABLE I-continued

Lymphocytic Leukemia P388 Test

| Compound | Dose (mg./kg.) | Median Survival (Days) | T/C × 100 (percent) |
| --- | --- | --- | --- |
| 5-Fluorouracil | 60 | 20.0 | 222 |
| 1,4-Bis[2-(2-hydroxyethylamino)ethylamino]-5,8-dihydroxyanthraquinone, tetrachloride, bis(chromium chloride chelate) | 25 | 30.0 | 333 |
|  | 12.5 | 30.0 | 333 |
|  | 6.25 | 30.0 | 333 |
|  | 3.12 | 22.0 | 244 |
|  | 1.56 | 20.0 | 222 |
| Control | 0 | 9.0 | — |
| 5-Fluorouracil | 60 | 20.0 | 222 |
| 1,4-Bis[2-(2-hydroxyethylamino)ethylamino]-5,8-dihydroxyanthraquinone, dinitrate, bis(cobalt nitrate chelate) | 12.5 | 16.5 | 183 |
|  | 6.25 | 26.0 | 289 |
|  | 3.12 | 30.0 | 333 |
|  | 1.56 | 23.0 | 256 |
| Control | 0 | 9.0 | — |
| 5-Fluorouracil | 60 | 20.0 | 222 |

Melanotic Melanoma B16

The animals used are C57BC/6 mice, all of the same sex, weighing a minimum of 17 g. and all within a 3 g. weight range. There are normally 10 animals per test group. A one gram portion of melanotic melanoma B16 tumor is homogenized in 10 ml. of cold balanced salt solution and a 0.5 ml. aliquot of the homogenate is implanted intraperitoneally into each of the test mice. The test compounds are administered intraperitoneally on days one, five and nine (relative to tumor inoculation) at various doses. The animals are weighed and survivors are recorded on a regular basis for 60 days. The median survival time and the ratio of survival time for treated (T)/control (C) animals are calculated. The positive control compound is 5-fluorouracil given as a 20 mg./kg. injection. The results of this test with a representative compound of the present invention appear in Table II. The criterion for efficacy is T/C×100≧125%.

TABLE II

Melanotic Melanoma B16 Test

| Compound | Dose (mg./kg.) | Median Survival (Days) | T/C × 100 (percent) |
| --- | --- | --- | --- |
| 1,4-Bis[2-(2-hydroxyethylamino)ethylamino]-5,8-dihydroxyanthraquinone, dichloride, bis-(platinum chloride chelate) | 12.0 | 55.0 | 355 |
|  | 6.0 | 50.5 | 326 |
|  | 3.0 | 35.5 | 229 |
|  | 1.5 | 28.5 | 184 |
|  | 0.7 | 22.0 | 142 |
|  | 0.3 | 21.0 | 135 |
| Control | 0 | 15.5 | — |
| 5-Fluorouracil | 20 | 23.0 | 148 |

A preferred embodiment of the present invention is represented by chelates of compounds of the following general formula:

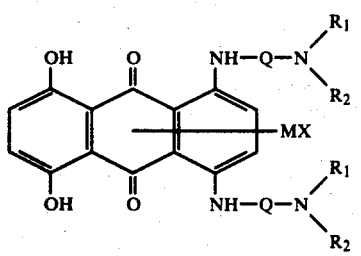

wherein Q, M and X are as hereinbefore defined; $R_1$ is hydrogen, alkyl having from 1 to 4 carbon atoms or monohydroxyalkyl having from 2 to 4 carbon atoms, with the proviso that the carbon atom alpha to the nitrogen atom does not bear an hydroxy group; $R_2$ is monohydroxyalkyl having from 2 to 4 carbon atoms, with the proviso that the carbon atom alpha to the nitrogen atom does not bear an hydroxy group, dihydroxyalkyl having from 3 to 6 carbon atoms, with the proviso that the carbon atom alpha to the nitrogen atom does not bear an hydroxy group or a moiety of the formula:

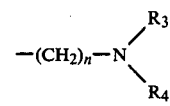

wherein N, $R_3$ and $R_4$ are as hereinbefore defined; with the proviso that the ratio of the total number of carbon atoms to the sum of the total number of oxygen atoms plus the total number of nitrogen atoms in each of the side chains at the 1-position and the 4-position does not exceed four. The preferred embodiment includes the corresponding leuco bases of the aromatic bases (I), the tautomers thereof, and the non-toxic pharmaceutically acceptable acid-addition salts thereof.

Another preferred embodiment of the present invention is represented by chelates of compounds of the following general formula:

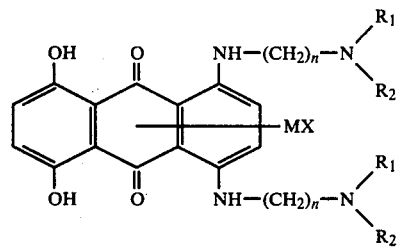

wherein n is an integer from 2 to 4, inclusive, and $R_1$ and $R_2$ are as defined for the preceding preferred embodiment with the proviso that the ratio of the total number of carbon atoms to the sum of the total number of oxygen atoms plus the total number of nitrogen atoms in each of the side chains at the 1-position and the 4-position may not exceed four. This preferred embodiment also includes the corresponding leuco bases for the aromatic bases (V), the tautomers thereof, and the non-toxic pharmaceutically acceptable acid-addition salts thereof.

Also embraced within the purview of the present invention are therapeutic compositions of matter containing chelates of certain 5,8-dihydroxy-1,4-bis(substituted-amino)-anthraquinones (or the leuco bases and non-toxic acid-salts thereof) which are represented by the following structural formula:

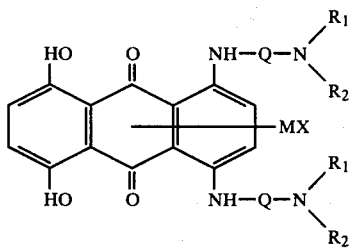

wherein $R_1$ is hydrogen or alkyl having from 1 to 4 carbon atoms, $R_2$ is hydrogen or alkyl having from 1 to 4 carbon atoms, $R_1$ and $R_2$ taken together with their associated nitrogen atom is as hereinbefore defined for $R_3$ and $R_4$ taken together with their associated nitrogen atom, and Q, M and X are as hereinbefore defined.

The active ingredients of the therapeutic compositions and the novel chelated compounds of the present invention inhibit transplanted mouse tumor growth when administered in amounts ranging from about 5 mg. to about 200 mg. per kilogram of body weight per day. A preferred dosage regimen for optimum results would be from about 5 mg. to about 50 mg. per kilogram of body weight per day, and such dosage units are employed that a total of from about 350 mg. to about 3.5 grams of the active compound for a subject of about 70 kg. of body weight are administered in a 24-hour period. This dosage regimen may be adjusted to provide the optimum therapeutic response. For example, several divided doses may be administered daily or the dose may be proportionally reduced as indicated by the exigencies of the therapeutic situation. A decided practical advantage is that the active compound may be administered in any convenient manner such as by the oral, intravenous, intramuscular, or subcutaneous routes.

The active chelated compounds may also be administered parenterally or intraperitoneally. Solutions of the active compound as a free base or pharmacologically acceptable salt can be prepared in water suitably mixed with a surfactant such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, a polyol (for example, glycerol, propylene glycol, liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired as herein disclosed in detail.

The principal active ingredient is compounded for convenient and effective administration in effective amounts with a suitable pharmaceutically-acceptable carrier in dosage unit form as hereinbefore disclosed. A unit dosage form can, for example, contain the principal active compound in amounts ranging from about 0.1 to about 400 mg., with from about one to about 30 mg. being preferred. Expressed in proportions, the active compound is generally present in from about 0.1 to about 400 mg./ml. of carrier. In the case of compositions containing supplementary active ingredients, the dosages are determined by reference to the usual dose and manner of administration of the said ingredients.

This invention will be described in greater detail in conjunction with the following specific examples.

EXAMPLE 1

Leuco-1,4-bis[(2-dimethylaminoethyl)-amino]-5,8-dihydroxy-anthraquinone

A reaction mixture comprising 10.58 g. of N,N-dimethylethylenediamine, 60 ml. of N,N,N',N'-tetramethylethylenediamine and 10.96 g. of leuco-1,4,5,8-tetrahydroxyanthraquinone is flushed with nitrogen and stirred under nitrogen for 2 hours while heating with an oil bath kept at 49°–51° C. The mixture is allowed to cool under nitrogen. The solid is collected and washed with ethanol giving 14.78 g. of the desired product as a dark red-brown solid.

EXAMPLE 2

1,4-Bis[(2-dimethylaminoethyl)amino]-5,8-dihydroxyanthraquinone

A 12.0 g. portion of leuco-1,4-bis[(2-dimethylaminoethyl)amino]-5,8-dihydroxyanthraquinone in 100 ml. of nitrobenzene is heated under reflux for 15 minutes and then filtered while hot. The filtrate is reheated to boiling, allowed to cool, and the solid is collected and washed with ethanol giving 8.44 g. of the desired product as blue-black crystals, m.p. 236°–238° C.

EXAMPLE 3

Leuco-1,4-bis(2-morpholinoethylamino)-5,8-dihydroxyanthraquinone

A solution of 15.62 g. of N-(2-aminoethyl)morpholine in 40 ml. of N,N,N',N'-tetramethylethylenediamine is de-aerated by bubbling nitrogen through it for 15 minutes. A 10.97 g. portion of leuco-1,4,5,8-tetrahydroxyanthraquinone is added slowly with stirring and the suspension is treated as described in Example 1, giving 18.07 g. of the desired product as an olive solid, m.p. 223°–227° C.

EXAMPLE 4

1,4-Bis(2-morpholinoethylamino)-5,8-dihydroxyanthraquinone

A 13.90 g. portion of leuco-1,4-bis(2-morpholinoethylamino)-5,8-dihydroxyanthraquinone in 100 ml. of nitrobenzene is oxidized as described in Example 2 giving 10.30 g. of the desired product as black rods, m.p. 241°–243° C.

EXAMPLE 5

Leuco-1,4-bis[(2-diethylaminoethyl)amino]-5,8-dihydroxyanthraquinone

The procedure of Example 3 is repeated using 13.95 g. of N,N-diethylethylenediamine in place of the N-(2-aminoethyl)-morpholine, giving 13.97 g. of the desired product as a red-brown solid, m.p. 182°–185° C.

EXAMPLE 6

1,4-Bis[(2-diethylaminoethyl)amino]-5,8-dihydroxyanthraquinone

A 10.90 g. portion of leuco-1,4-bis[(2-diethylaminoethyl)amino]-5,8-dihydroxyanthraquinone is oxidized as described in Example 2 giving 6.35 g. of the desired product as blue-black needles, m.p. 202°–204° C.

EXAMPLE 7

Leuco-1,4-bis[2-(1-pyrrolidinyl)ethylamino]-5,8-dihydroxyanthraquinone

The procedure of Example 3 is repeated using 12.05 g. of N-2-pyrrolidinoethylamine, in place of the N-(2-aminoethyl)-morpholine, and 80 ml. of N,N,N',N'-tetramethylethylenediamine, giving 13.24 g. of the desired product as a red-brown solid, m.p. 180°–185° C.

EXAMPLE 8

1,4-Bis[2-(1-pyrrolidinyl)ethylamino]-5,8-dihydroxyanthraquinone

An 8.61 g. portion of leuco-1,4-bis[[2-(1-pyrrolidinyl)ethyl]amino]-5,8-dihydroxyanthraquinone is oxidized as described in Example 2. The reaction mixture is evaporated to dryness and the residue recrystallized from toluene, giving 5.12 g. of the desired product as blue-black crystals, m.p. 193°–196° C.

EXAMPLE 9

Leuco -1,4-bis[2-(methylamino)ethylamino]-5,8-dihydroxyanthraquinone

The procedure of Example 7 is repeated using 8.90 g. of N-methylethylenediamine in place of the N-2-pyrrolidinoethylamine, giving 13.73 g. of the desired product as a dark green solid, m.p. 157°–160° C.

EXAMPLE 10

Leuco-1,4-bis[(3-dimethylaminopropyl)amino]-5,8-dihydroxyanthraquinone

Nitrogen is bubbled through an 80 ml. portion of dimethylaminopropylamine for 15 minutes. A 10.97 g. portion of leuco-1,4,5,8-tetrahydroxyanthraquinone is added slowly with stirring. The mixture is heated under nitrogen at 50°–52° C. for 2 hours and then allowed to cool. The solid is collected and washed with cold ethanol giving 5.59 g. of dark, orange-red crystals, m.p. 115°–118° C.

EXAMPLE 11

1,4-Bis[(3-dimethylaminopropyl)amino]-5,8-dihydroxyanthraquinone

A suspension of 6.00 g. of leuco-1,4-bis[(3-dimethylaminopropyl)amino]-5,8-dihydroxyanthraquinone in 60 ml. of N,N,N',N'-tetramethylethylenediamine is heated on a steam bath under reflux while air is bubbled in for 12 hours. The solution is cooled, producing a solid which is collected and washed twice with heptane and once with petroleum ether. This solid is recrystallized by extracting with 350 ml. of hot heptane, filtering and concentrating to 300 ml. Crystallization and washing with petroleum ether gives 3.72 g. of the desired product as black needles, m.p. 154°–157° C.

EXAMPLE 12

Leuco-1,4-bis(2-aminoethylamino)-5,8-dihydroxyanthraquinone

A reaction mixture comprising 10.97 g. of leuco-1,4,5,8-tetrahydroxyanthraquinone in 80 ml. of de-aerated N,N,N',N'-tetramethylethylenediamine containing 7.22 g. of ethylenediamine is heated and stirred under nitrogen at 48°–50° C. for one hour. The mixture is allowed to stand under a slow flow of nitrogen, producing a solid which is collected and washed with ethyl acetate, acetonitrile and petroleum ether giving 13.8 g. of the desired product as a red-black solid.

EXAMPLE 13

Leuco-1,4-bis(3-aminopropylamino)-5,8-dihydroxyanthraquinone

A suspension of 10.97 g. of leuco-1,4,5,8-tetrahydroxyanthraquinone in a de-aerated solution of 8.90 g. of 1,3-diaminopropane in 80 ml. of N,N,N',N'-tetramethylethylenediamine is stirred and heated at 49° C. for one hour under nitrogen, then allowed to cool. The resulting solid is collected and washed with cold ethanol giving 14.21 g. of the desired product as a black solid.

EXAMPLE 14

Leuco-1,4-bis[2-(2-hydroxyethylamino)ethylamino]-5,8-dihydroxyanthraquinone

A suspension of 12.5 g. of 2-(2-aminoethylamino)-ethanol in 40 ml. of N,N,N'N'-tetramethylethylenediamine is stirred and de-aerated by bubbling nitrogen in for 15 minutes. A 10.97 g. portion of leuco-1,4,5,8-tetrahydroxyanthraquinone is gradually added with stirring. The suspension is heated and stirred under nitrogen in an oil bath at 50°-52° C. for 5 hours. The mixture is allowed to stand and cool under nitrogen for 12 hours. The solid is collected by decantation, macerated in ethanol, collected and washed with ethanol giving 15.06 g. of the desired product as a green-gray solid, m.p. 129°-131° C.

EXAMPLE 15

Leuco-1,4-bis[2-[di($\beta$-hydroxyethyl)amino]ethylamino]-5,8-dihydroxyanthraquinone A solution of 17.8 g. of N,N-di(2-hydroxyethyl)-ethylenediamine in 100 ml. of methanol is cooled with an ice bath, stirred, and de-aerated by bubbling in nitrogen for 15 minutes. A 10.97 g. portion of leuco-1,4,5,8-tetrahydroxyanthraquinone is gradually added with stirring and continued cooling. The suspension is heated and stirred under nitrogen in an oil bath at 50°-52° C. for one hour and the mixture is then allowed to stand and cool under nitrogen overnight. The solid is collected and washed with ethanol giving 14.8 g. of a red-brown solid, m.p. 165°-168° C.

EXAMPLE 16

1,4-Bis[2-(methylamino)ethylamino]-5,8-dihydroxyanthraquinone dihydrochloride

To a suspension of 11.60 g. of leuco-1,4-bis[2-(methylamino)ethylamino]-5,8-dihydroxyanthraquinone in 200 ml. of 2-methoxyethanol is added gradually with stirring 15 ml. of 8 N ethanolic hydrogen chloride. The system is chilled with an ice bath and stirred as 7.50 g. of chloranil powder is gradually added. The mixture is stirred overnight at room temperature and diluted with 600 ml. of ether. The solid is collected and washed with tetrahydrofuran. The product (14.16 g.) is recrystallized by dissolving it in 130 ml. of water and adding 650 ml. of acetone to give 13.15 g. of a blue-black solid.

EXAMPLE 17

1,4-Bis[2-(2-aminoethylamino)ethylamino]-5,8-dihydroxyanthraquinone

Following the general procedure of Example 3, a mixture of 10.97 g. of leuco-1,4,5,8-tetrahydroxyanthraquinone, 80 ml. of N,N,N',N'-tetramethylethylenediamine and 21.84 g of diethylenetriamine gives a thick, congealed mass which prevents effective stirring so the reaction time is extended to 24 hours. The mixture is allowed to cool and the supernatent liquid is decanted and discarded. A solution of the congealed mass in 100 ml. of methanol is filtered, then allowed to oxidize in the air for four days in a partially covered flask. The gelatinous mass which separates becomes solid when the oxidation mixture is agitated with 200 ml. of acetonitrile and then allowed to stand for one hour. After the solid is collected and washed first with acetonitrile, then with ether, the yield is 10.88 g. of a blue-black powder.

EXAMPLE 18

Leuco-1,4-bis(4-aminobutylamino)-5,8-dihydroxyanthraquinone

Following the general procedure of Example 3 but using 45 ml. of 1,4-diaminobutane as the primary amine component, there is obtained 12.20 g. of product as a dull grey-green solid.

EXAMPLE 19

Leuco-1,4-bis[2-dimethylaminopropylamino]-5,8-dihydroxyanthraquinone

The reaction of 12.26 g. of 2-dimethylaminopropylamine with 10.97 g. of leuco-1,4,5,8-tetrahydroxyanthraquinone in 100 ml. of ethanol for one hour by the procedure of Example 1 gives 7.29 g. of red-brown crystals.

EXAMPLE 20

Leuco-1,4-bis[2-(2-methylaminoethylamino)ethylamino]5,8-dihydroxyanthraquinone

To a solution of 14.10 g. of 1-methyl diethylenetriamine in 50 ml. of ethanol and 40 ml. of N,N,N',N'-tetramethylethylenediamine is added 10.97 g. of leuco-1,4,5,8-tetrahydroxyanthraquinone as in Example 1. The mixture is heated at 50° C. and stirred under nitrogen for one hour, chilled with an ice bath, the solid collected and washed with cold ethanol to give 7.23 g. of green-black crystals, m.p. 108°-111° C.

EXAMPLE 21

Leuco-1,4-bis[2-(2-dimethylaminoethylamino)ethylamino]-5,8-dihydroxyanthraquinone The reaction of N-(dimethylaminoethyl)ethylenediamine with leuco-1,4,5,8-tetrahydroxyanthraquinone by the procedure of Example 20 gives the title compound.

EXAMPLE 22

Leuco-1,4-bis[2-(1-piperazinyl)ethylamino]-5,8-dihydroxyanthraquinone

The procedure of Example 20 applied to 15.50 g of N-(2-aminoethyl)piperazine gives 3.92 g. of a black powder which does not melt by 350° C. and is discarded. The mother liquor and ethanol washes, on standing and partly evaporating during two weeks in an unstoppered flask, deposit a solid which is collected and washed with ethanol to give 6.19 g. of the title compound as a black solid, m.p. 200°–203° C.

EXAMPLE 23

1,4-Bis(2-aminoethylamino)-5,8-dihydroxyanthraquinone dihydrochloride

Oxidation with chloranil of 28.25 g. of the product of Example 12 by the procedure of Example 16 gives 29.66 g. of a crude, blue-black solid which is then extracted by stirring for 14 hours with 800 ml. of water. Solids are removed by centrifugation and the supernatant solution freeze-dried, leaving 16.38 g. of a blue-black solid which is unmelted by 350° C.

EXAMPLE 24

1,4-Bis[2-(2-hydroxyethylamino)ethylamino]-5,8-dihydroxyanthraquinone Dihydrochloride Chloranil oxidation of 17.86 g. of the product of Example 14 by the procedure of Example 16 gives (without recrystallization) 21.34 g. of blue-black solid, m.p. 203°–205° C.

EXAMPLE 25

1,4-Bis[2-(2-methylaminoethylamino)ethylamino]-5,8-dihydroxyanthraquinone Tetrahydrochloride The product of Example 20 (11.70 g.) is oxidized with chloranil by the procedure of Example 16, giving 18.03 g. of blue-black solid, m.p. 190°–203° C.

EXAMPLE 26

1,4-Bis[2-(2-hydroxyethylamino)ethylamino]-5,8-dihydroxyanthraquinone

In a modification of the synthesis of Example 14 the solvent used is 100 ml. of ethanol. The mother liquor from the leuco product is allowed to stand for two weeks in an unstoppered flask, whereupon the oxidized product separates. It is collected and washed with ethanol, then recrystallized from ethanol, giving blue-black crystals, m.p. 175°–177° C.

EXAMPLE 27

Leuco-1,4-bis[3-(2-hydroxyethylamino)-1-propylamino]-5,8-dihydroxyanthraquinone

The procedure of Example 15 is used with a solution of 14.18 g. of 2-(3-aminopropylamino)ethanol in 100 ml. of ethanol. The resulting solution is filtered and the filtrate diluted with 300 ml. of ether, precipitating the product as a semi-solid. After decantation of the supernatant solution the semi-solid is caused to crystallize by agitating it with 100 ml. of tetrahydrofuran. Washing with ethanol gives 12.56 g. of green-black solid, m.p. 101°–104° C.

EXAMPLE 28

1,4-Bis[3-(2-hydroxyethylamino)-1-propylamino]-5,8-dihydroxyanthraquinone dihydrochloride Oxidation of 9.95 g. of leuco-1,4-bis[3-(2-hydroxyethylamino)propylamino]-5,8-dihydroxyanthraquinone with chloranil as in Example 16 gives 11.70 g. of a blue solid which does not melt by 350° C.

EXAMPLE 29

Leuco-1,4-bis[2-(3-hydroxy-1-propylamino)ethylamino]-5,8-dihydroxyanthraquinone

The procedure of Example 15 is paralleled with 14.18 g. of N-(3-hydroxypropyl)ethylenediamine in 100 ml. of ethanol to give 14.63 g. of red-brown crystals, m.p. 58°–60° C.

EXAMPLE 30

1,4-Bis[2-(3-hydroxy-1-propylamino)ethylamino]-5,8-dihydroxyanthraquinone dihydrochloride Chloranil oxidation of 10.77 g. of the product of Example 29 by the procedure of Example 16 yields 11.64 g. of a dark blue solid, m.p. 210°–216° C.

EXAMPLE 31

Leuco-1,4-bis[2-(2-hydroxy-1-propylamino)ethylamino]-5,8-dihydroxyanthraquinone

With 14.18 g. of 1-(2-aminoethylamino)-2-propanol in 100 ml. of ethanol the procedure of Example 15 yields 17.61 g. of green-black crystals, m.p. 50°–60° C.

EXAMPLE 32

1,4-Bis[2-(2-hydroxy-1-propylamino)ethylamino]-5,8-dihydroxyanthraquinone dihydrochloride A filtered solution of 14.44 g. of leuco-1,4-bis[2-(2-hydroxy-1-propylamino)ethylamino]-1,4-dihydroxyanthraquinone in 215 ml. of 2-methoxyethanol is oxidized with 7.65 g. of chloranil by the procedure of Example 16, affording 16.75 g. of purple solid, m.p. 177°–185° C.

EXAMPLE 33

Leuco-1,4-bis[2-[2-(2-hydroxyethylamino)ethylamino]-5,8-dihydroxyanthraquinone

The procedure of Example 15 used with a solution of 17.67 g. of 2-[2-(2-aminoethylamino)ethylamino]ethanol in 100 ml. of methanol gives a solution which is filtered, then diluted with 300 ml. of ether, precipitating a semi-solid which hardens on standing overnight. Hardening is completed by thorough maceration of the solid in the solvent. The solid is collected and washed with ether, yielding 16.82 g. of a green-black solid. This solid remains granular if stored at −25° C., but coalesces into a solid cake if stored at 25° C.

EXAMPLE 34

1,4-Bis[2-[2-(2-hydroxyethylamino)ethylamino]-ethylamino]-5,8-dihydroxyanthraquinone tetrahydrochloride Chloranil oxidation of 12.10 g. of the product of Example 33 by the method of Example 16, including three additional washings of the solid with methanol, gives 12.46 g. of dark blue, solid product.

EXAMPLE 35

1,4-Bis[2-(2,3-dihydroxypropylamino)ethylamino]-5,8-dihydroxyanthraquinone dihydrochloride By the procedure of Example 15 a solution of 16.10 g. of 3-(2-aminoethylamino)-1,2-propanediol [A. R. Surrey, C. M. Suter and J. S. Buck, J. A. C. S., 74, 4102(1952)] in 100 ml. of methanol gives a semi-solid which is separated from solvent by chilling with an ice bath, then decanting. The semi-solid is washed four times by stirring 1.5 hours at 25° C. with 100 ml. portions of methanol, chilling with an ice bath, then decanting. A filtered solution of the semi-solid in 280 ml. of 2-methoxyethanol is oxidized with 10.01 g. of chloranil by the method of Example 16. The product is additionally washed with ethanol, giving 15.25 g. of a blue-black solid, m.p. 191°–193° C.

EXAMPLE 36

Leuco-1,4-bis[2-(1-aziridino)ethylamino]-5,8-dihydroxyanthraquinone

With 10.33 g. of N-(2-aminoethyl)aziridine in 80 ml. of N,N,N',N'-tetramethylethylenediamine the procedure of Example 15 gives a stiff gum. The next day the supernatant solution is discarded, 100 ml. of ether is added and the gum periodically macerated therein for another day, when the gum is mostly hardened. Hardening is completed by maceration during three washings of the solid with ether, giving 12.66 g. of blue-black, granular powder.

EXAMPLE 37

1,4-Bis[2-(1-aziridino)ethylamino]-5,8-dihydroxyanthraquinone

To a suspension of 4.10 g. of the product of Example 36 in 40 ml. of chloroform is added a solution of 1.74 g. of diethyl azodicarboxylate in 25 ml. of chloroform. The mixture is stirred for 20 minutes, the resulting dark blue solution is filtered, and the filtrate is evaporated at >30° C. A solution of the residue in 40 ml. of chloroform is stirred five minutes with 2 g. of decolorizing carbon, filtered and washed through with another 25 ml. of chloroform. Addition of 100 ml. of ether to the filtrates precipitates a gum which is eliminated by decantation-filtration. The filtrates deposit crystals which are washed sparingly with acetone. The chloroform-ether mother liquor, chilled at −60° C., deposits a second crop of crystals which is washed with ether and with methanol. A solution of both crops of crystals in 20 ml. of chloroform is stirred with decolorizing carbon, filtered, evaporated at >25° C. to a volume of 5 ml., diluted with 20 ml. of ether, then chilled at −60° C. The resulting blue-black crystals, washed with ether, amount to 0.64 g., m.p. 168°–170° C. In thin-layer chromatography on silica gel the product is moved as a blue spot by chloroform-triethylamine-methanol, 27/3/1 (ratios by volume).

EXAMPLE 38

1,4-Bis[2-[2-(1-morpholino)ethylamino]ethylamino]-5,8-dihydroxyanthraquinone tetrahydrochloride A solution of 20.80 g. of N-(morphlinoethyl)ethylenediamine in 100 ml. of ethanol is used as described in Example 15 to give a solution which is filtered and diluted with 900 ml. of ether, precipitating a semi-solid. The supernatent solution is decanted, the semi-solid dissolved in 175 ml. of 2-methoxyethanol and oxidized with 5.29 g. of chloranil by the method of Example 16, giving 17.7 g. of dark blue solid.

EXAMPLE 39

Leuco-1,4-Bis[2-(acetamido)ethylamino]-5,8-dihydroxyanthraquinone

A solution of 12.26 g. of N-acetylethylene diamine in 100 ml. of ethanol in the procedure of Example 15 gives 15.27 g. of dark, red-brown solid, m.p. 125° C.

EXAMPLE 40

1,4-Bis[2-(acetamido)ethylamino]-5,8-dihydroxyanthraquinone

A suspension of 11.95 g. of leuco-1,4-bis[2-(acetamido)ethylamino]-5,8-dihydroxyanthraquinone is oxidized with 6.76 g. of chloranil during 61 hours by the method of Example 16, giving a very acidic hydrochloride salt which is converted to the free base by four washings with water. Crystallization from 110 ml. of dimethyl sulfoxide (boiling only 2 minutes and not attempting a hot filtration), then washing with dimethyl sulfoxide and with ethanol gives 7.76 g. of blue-black solid, m.p. 273°–274° C.

EXAMPLE 41

1,4-Bis[2-[N-(2-hydroxyethyl)trifluoroacetamido]-ethylamino]-5,8-dihydroxyanthraquinone A suspension of 1.50 g. of 1,4-bis[2-(2-hydroxyethylamino)ethylamino]-5,8-dihydroxyanthraquinone in 75 ml. of ethyl trifluoroacetate and 75 ml. of methanol is stirred for 10 minutes. Evaporation of the resulting solution in vacuo at 30° C. leaves a residue which is washed and macerated with methylene chloride, giving 2.11 g. of blue-black solid, m.p. 162° C.

EXAMPLE 42

1,4-Bis[2-amino-2-carboxyethylamino]-5,8-dihydroxyanthraquinone .¾ HCl

To a solution of 6.23 g. of dl-α,β-diaminopropionic acid in 30 ml. of warm water is added 1.078 g. of lithium hydroxide and 60 ml. of dimethyl sulfoxide. The system is flushed with nitrogen and 4.12 g. of leuco-1,4,5,8-tetrahydroxyanthraquinone is added gradually with stirring. The mixture is stirred and heated with an oil bath at 50° C., first for 15 hours under nitrogen, then for 21 hours as the initial product is oxidized by bubbling in a stream of air. Thin-layer chromatography on silica gel with methanol-water-concentrated ammonia (25/5/1 by volume) shows all the product spots to be blue when the oxidation is complete. After the mixture is cool the solids are removed by filtration and washed once with dimethyl sulfoxide-water (2/1). Addition of 400 ml. of methanol to the filtrates precipitates a solid which is collected and washed with methanol. Further washing with a total of 13 ml. of 0.01 N aqueous acetic acid dissolves virtually all of the solid. Addition of 3 ml. of concentrated hydrochloric acid to the acetic acid filtrates precipitates a blue-black solid which is washed with acetone to give 0.24 g. of the product.

EXAMPLE 43

Leuco-1,4-bis[2-(2-methoxyethylamino)ethylamino]-5,8-dihydroxyanthraquinone

An ethanol solution of N-(2-methoxyethyl)ethylenediamine (U.S. Pat. No. 3,454,640) reacts in the procedure of Example 15 to give the title compound.

EXAMPLE 44

1,4-Bis[2-(1,3-oxazolidin-1-yl)ethylamino]-5,8-dihydroxyanthraquinone

A solution of 1.62 g. of 37% aqueous formaldehyde solution in 50 ml. of water is stirred overnight with 4.44 g. of 1,4-bis[2-(2-hydroxyethylamino)ethylamino]-5,8-dihydroxyanthraquinone. The resulting solid is washed with water to give the product.

EXAMPLE 45

1,4-Bis[2-(tetrahydro-1,3-oxazin-1-yl)ethylamino]-5,8-dihydroxyanthraquinone

A solution of 1.62 ml. of 37% aqueous formaldehyde in 50 ml. of 0.4 N aqueous sodium hydroxide is stirred overnight with 5.45 g. of 1,4-bis[2-(3-hydroxy-1-propylamino)-ethylamino]-5,8-dihydroxyanthraquinone dihydrochloride. The product is obtained by washing the resulting solid with water.

EXAMPLE 46

1,4-Bis[2-(1,3-oxazolidin-2-one-1-yl)ethylamino]-5,8-dihydroxyanthraquinone

A solution of 0.020 g. of sodium in 25 ml. of methanol is stirred and heated under reflux overnight with 75 ml. of diethyl carbonate and 4.44 g. of 1,4-bis[2-(2-hydroxyethylamino)ethylamino]-5,8-dihydroxyanthraquinone. The mixture is allowed to cool. It is stirred with 0.1 ml. of acetic acid, the solid is collected by filtration and washed with methanol to give the product.

EXAMPLE 47

1,4-Bis[2-(1,3-oxazin-2-one-1-yl)ethylamino]-5,8-dihydroxyanthraquinone

A solution of 0.48 g. of sodium in 25 ml. of methanol is stirred and heated overnight with 75 ml. of diethyl carbonate and 5.45 g. of 1,4-bis[2-(3-hydroxy-1-propylamino)ethylamino]-5,8-dihydroxyanthraquinone dihydrochloride. After the mixture cools it is stirred with 0.1 ml. of acetic acid. The solid product is collected by filtration and washed with methanol and then with water.

EXAMPLE 48

1,4-Bis[2-[di($\beta$-hydroxyethyl)amino]ethylamino]-5,8-dihydroxyanthraquinone dihydrochloride Chloranil oxidation of 10.77 g. of the product of Example 15 by the method of Example 16 gives 11.64 g. of a dark blue solid, m.p. 216° C.

EXAMPLE 49

1,4-Bis[2-(2-hydroxyethylamino)ethylamino]-5,8-dihydroxyanthraquinone disuccinate salt A mixture of 222 mg. of 1,4-bis[2-(2-hydroxyethylamino)ethylamino]-5,8-dihydroxyanthraquinone, 118 mg. of succinic acid, and 50 ml. of ethanol is heated under reflux for 30 minutes to give the title compound.

EXAMPLE 50

1,4-Bis[2-(3-hydroxypropylamino)ethylamino]-5,8-dihydroxyanthraquinone dimalate salt A mixture of 228 mg. of 1,4-bis[2-(3-hydroxypropylamino)ethylamino]-5,8-dihydroxyanthraquinone, 134 mg. of DL-malic acid, and 50 ml. of ethanol is heated under reflux for 30 minutes to give the title compound.

EXAMPLE 51

1,4-Bis[2-(2-hydroxypropylamino)ethylamino]-5,8-dihydroxyanthraquinone dilactate salt A mixture of 228 mg. of 1,4-bis[2-(2-hydroxypropylamino)ethylamino]-5,8-dihydroxyanthraquinone, 120 mg. of 80% DL-lactic acid, and 10 ml. of ethanol is heated on a steam bath for 10 minutes, cooled, treated with 50 ml. of acetone and cooled to obtain the title compound.

EXAMPLE 52

1,4-Bis[2-(3-hydroxypropylamino)ethylamino]-5,8-dihydroxyanthraquinone diacetate salt A mixture of 228 mg. of 1,4-bis[2-(3-hydroxypropylamino)ethylamino]-5,8-dihydroxyanthraquinone, 60 mg. of glacial acetic acid, and 50 ml. of ethanol is heated under reflux for 30 minutes to give the title compound.

EXAMPLE 53

1,4-Bis[2-(2-hydroxypropylamino)ethylamino]-5,8-dihydroxyanthraquinone diacetate salt A mixture of 228 mg. of 1,4-bis[2-(2-hydroxypropylamino)ethylamino]-5,8-dihydroxyanthraquinone, 60 mg. of glacial acetic acid, and 10 ml. of ethanol is heated on a steam bath for 10 minutes, cooled, treated with 50 ml. of acetone and cooled to obtain the title compound.

EXAMPLE 54

1,4-Bis[2-(2-hydroxyethylamino)ethylamino]-5,8-dihydroxyanthraquinone, tetrachloride, bis(dicyclopentadienyl zirconium chelate)

A 1.0 g. portion of 1,4-bis[2-(2-hydroxyethylamino)ethylamino]-5,8-dihydroxyanthraquinone dihydrochloride and 220 mg. of potassium hydroxide are dissolved in 25 ml. of ethanol. A 1.1 g. portion of zirconocene dichloride is added and the mixture is refluxed for 6 hours, cooled and filtered, giving 1.5 g. of the desired product as a blue powder, m.p. >350° C.

EXAMPLE 55

1,4-Bis[2-(2-hydroxyethylamino)ethylamino]-5,8-dihydroxyanthraquinone, tetrachloride, bis(chromium chloride chelate)

A 1.0 g. portion of 1,4-bis[2-(2-hydroxyethylamino)ethylamino]-5,8-dihydroxyanthraquinone dihydrochloride and 220 mg. of potassium hydroxide are dissolved in methanol. A 1.08 g. portion of chromic chloride hexahydrate is added and the mixture is refluxed for 6 hours, cooled and filtered, giving 900 mg. of the desired product as blue-purple cubes.

EXAMPLE 56

1,4-Bis[2-(2-hydroxyethylamino)ethylamino]-5,8-dihydroxyanthraquinone, dinitrate, bis(cobalt nitrate chelate)

A 1.0 g. portion of 1,4-bis[2-(2-hydroxyethylamino)ethylamino]-5,8-dihydroxyanthraquinone dihydrochloride and 220 mg. of potassium hydroxide are dissolved in methanol. A 1.2 g. portion of cobalt nitrate hexahydrate is added and the mixture is refluxed for 6 hours, cooled and filtered, giving 900 mg. of the desired product as a dark blue solid.

EXAMPLE 57

1,4-Bis[2-(2-hydroxyethylamino)ethylamino]-5,8-dihydroxyanthraquinone, dichloride, bis(platinum chloride chelate)

A mixture of 1,4-bis[2-(2-hydroxyethylamino)ethylamino]-5,8-dihydroxyanthraquinone dihydrochloride, potassium hydroxide and platinum chloride in methanol is reacted as described in Example 54, giving 500 mg. of the desired product as a blue solid.

EXAMPLE 58

1,4-Bis[2-(2-hydroxyethylamino)ethylamino]-5,8-dihydroxyanthraquinone, dichloride, bis(cuprous chloride chelate)

A mixture of 1,4-bis[2-(2-hydroxyethylamino)ethylamino]-5,8-dihydroxyanthraquinone dihydrochloride, potassium hydroxide and cuprous chloride in methanol is reacted as described in Example 54, giving 500 mg. of the desired product as a black solid.

EXAMPLE 59

1,4-Bis[2-(2-hydroxyethylamino)ethylamino]-5,8-dihydroxyanthraquinone, dichloride, bis(ferric chloride chelate)

A mixture of 1,4-bis[2-(2-hydroxyethylamino)ethylamino]-5,8-dihydroxyanthraquinone dihydrochloride, potassium hydroxide and ferric chloride in methanol is reacted as described in Example 54, giving 500 mg. of the desired product as a blue solid.

EXAMPLE 60

1,4-Bis[2-(2-hydroxyethylamino)ethylamino]-5,8-dihydroxyanthraquinone, trisulfate, tris(zinc chelate)

A mixture of 1,4-bis[2-(2-hydroxyethylamino)ethylamino]-5,8-dihydroxyanthraquinone dihydrochloride, potassium hydroxide and zinc sulfate septahydrate in methanol is reacted as described in Example 54, giving the desired product.

EXAMPLE 61

Leuco-1,4-bis[(2-dimethylaminoethyl)amino]-5,8-dihydroxyanthraquinone bis(ferric chloride chelate)

A mixture of leuco-1,4-bis[(2-dimethylaminoethyl)amino]-5,8-dihydroxyanthraquinone dihydrochloride and ferric chloride in ethanol is reacted as described in Example 54 to give the desired product.

EXAMPLE 62

1,4-Bis[(2-dimethylaminoethyl)amino]-5,8-dihydroxyanthraquinone, dihydrochloride, bis(zinc sulfate chelate)

A mixture of 1,4-bis[(2-dimethylaminoethyl)amino]-5,8-dihydroxyanthraquinone dihydrochloride and zinc sulfate in ethanol-water is reacted as described in Example 54 with the following exception. The product is isolated by solvent removal.

EXAMPLE 63

1,4-Bis(2-morpholinoethylamino)-5,8-dihydroxyanthraquinone, dihydrochloride, palladium chloride chelate A mixture of 1,4-bis(2-morpholinoethylamino)-5,8-dihydroxyanthraquinone dihydrochloride, potassium hydroxide, and potassium tetrachloropalladate in methanol is refluxed for 3 hours. Cooling, concentration and filtration gives the desired product.

EXAMPLE 64

1,4-Bis[(2-methylamino)ethylamino]-5,8-dihydroxyanthraquinone dihydrochloride bis(cobalt chloride chelate)

A mixture of 1,4-bis[(2-methylamino)ethylamino]-5,8-dihydroxyanthraquinone dihydrochloride and cobalt chloride hexahydrate in ethanol is refluxed for 4 hours. The product is isolated by solvent removal.

EXAMPLE 65

1,4-Bis[2-(2,3-dihydroxypropylamino)ethylamino]-5,8-dihydroxyanthraquinone dihydrochloride tris(platinum chloride chelate)

A mixture of 1,4-bis[2-(2,3-dihydroxypropylamino)ethylamino]-5,8-dihydroxyanthraquinone dihydrochloride and potassium tetrachloroplatinate in ethanol-water is refluxed for 3 hours. Concentration and cooling gives the desired product.

EXAMPLE 66

1,4-Bis[2-(2-hydroxyethylamino)ethylamino]-5,8-dihydroxyanthraquinone dihydrochloride, tris(chromium chloride chelate)

This material is prepared as described in Example 2 with an adjusted amount of chromium chloride hexahydrate.

EXAMPLE 67

1,4-Bis[2-(2-hydroxyethylamino)ethylamino]-5,8-dihydroxyanthraquinone dihydrochloride tris(cobalt chloride chelate)

A mixture of 1,4-bis[2-(2-hydroxyethylamino)ethylamino]-5,8-dihydroxyanthraquinone dihydrochloride and cobalt chloride hexahydrate in ethanol-water is refluxed for 2 hours. Concentration and cooling gives the desired blue solid.

EXAMPLE 68

1,4-Bis[2-(2-hydroxyethylamino)ethylamino]-5,8-dihydroxyanthraquinone dihydrochloride, tris(platinum chloride chelate)

A mixture of 1,4-bis[2-(2-hydroxyethylamino)ethylamino]-5,8-dihydroxyanthraquinone dihydrochloride and potassium tetrachloroplatinate is refluxed in ethanol for 2 hours. Cooling and filtration gives the desired black solid.

EXAMPLE 69

1,4-Bis[2-(2-hydroxyethylamino)ethylamino]-5,8-dihydroxyanthraquinone tris(iron chelate)

A mixture of 1,4-bis[2-(2-hydroxyethylamino)ethylamino]-5,8-dihydroxyanthraquinone, potassium hydroxide and ferric chloride hexahydrate in ethanol-water is refluxed for 3 hours. Solvent removal gives the product.

EXAMPLE 70

1,4-Bis[2-(acetamido)ethylamino]-5,8-dihydroxyanthraquinone, tris(zinc sulfate complex)

A mixture of 1,4-bis[2-(acetamido)ethylamino]-5,8-dihydroxyanthraquinone, and zinc sulfate heptahydrate in methanol is refluxed for 6 hours. Concentration and cooling gives the desired material.

We claim:

1. A chelated compound selected from the group consisting of those of the formula:

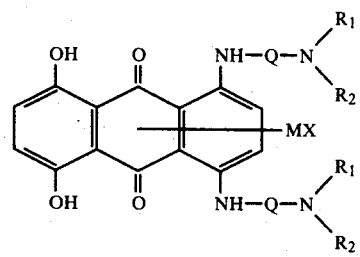

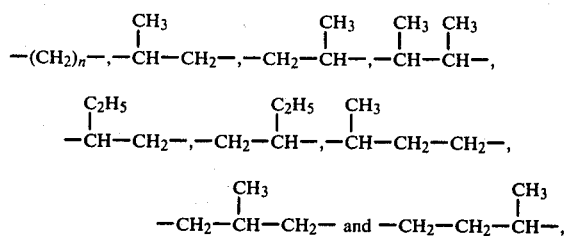

wherein Q is a divalent moiety selected from the group consisting of those of the formulae:

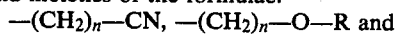

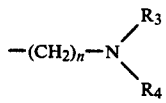

wherein n is an integer from 2 to 4 inclusive; $R_1$ and $R_2$ are each individually selected from the group consisting of hydrogen, alkyl($C_1$-$C_4$), monohydroxyalkyl($C_1$-$C_4$), with the proviso that the carbon atom alpha to the nitrogen atom does not bear an hydroxy group, dihydroxyalkyl($C_3$-$C_6$), with the proviso that the carbon atom alpha to the nitrogen atom does not bear an hydroxy group, formyl, alkanoyl($C_2$-$C_4$), trifluoroacetyl and moieties of the formulae:

—$(CH_2)_n$—CN, —$(CH_2)_n$—O—R and

wherein n is an integer 2 to 4 inclusive, R is alkyl($C_1$-$C_4$) and $R_3$ and $R_4$ are each individually selected from the group consisting of hydrogen, alkyl($C_1$-$C_4$) and monohydroxyalkyl($C_2$-$C_4$), with the proviso that the carbon atom alpha to the nitrogen atom does not bear an hydroxy group and the group

is morpholino, thiomorpholino, piperazino, 4-methyl-1-piperazino or a moiety of the formula:

wherein m is an integer 2 to 6 inclusive; with the proviso that the ratio of the total number of carbon atoms to the sum of the total number of oxygen atoms plus the total number of nitrogen atoms in the side chains at the 1-position and the 4-position does not exceed 4 and with the further proviso that $R_1$ and $R_2$ are not both hydrogen or alkyl; M is selected from the group platinum, copper, iron, zirconium, cobalt, chromium and zinc; X is chloride, sulfate or nitrate and the pharmacologically acceptable acid-addition salts thereof.

2. A chelated compound selected from the group consisting of those of the formula:

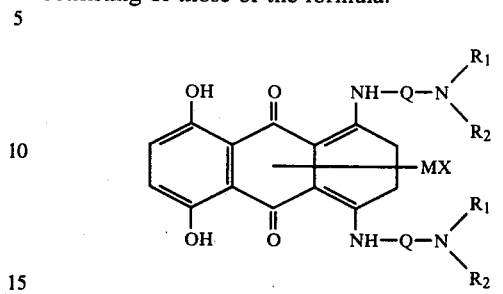

wherein Q is a divalent moiety selected from the group consisting of those of the formulae:

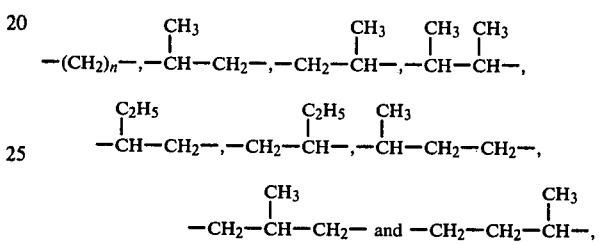

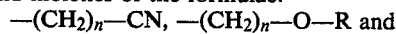

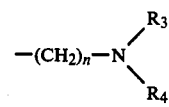

wherein n is an integer from 2 to 4 inclusive; $R_1$ and $R_2$ are each individually selected from the group consisting of hydrogen, alkyl($C_1$-$C_4$), monohydroxyalkyl($C_1$-$C_4$), with the proviso that the carbon atom alpha to the nitrogen atom does not bear an hydroxy group, dihydroxyalkyl($C_3$-$C_6$), with the proviso that the carbon atom alpha to the nitrogen atom does not bear an hydroxy group, formyl, alkanoyl($C_2$-$C_4$), trifluoroacetyl and moieties of the formulae:

—$(CH_2)_n$—CN, —$(CH_2)_n$—O—R and

wherein n is an integer 2 to 4 inclusive, R is alkyl($C_1$-$C_4$) and $R_3$ and $R_4$ are each individually selected from the group consisting of hydrogen, alkyl($C_1$-$C_4$) and monohydroxyalkyl($C_2$-$C_4$), with the proviso that the carbon atom alpha to the nitrogen atom does not bear an hydroxy group and the group

is morpholino, thiomorpholino, piperazino, 4-methyl-1-piperazino or a moiety of the formula:

wherein m is an integer 2 to 6 inclusive; with the proviso that the ratio of the total number of carbon atoms to the sum of the total number of oxygen atoms plus the total number of nitrogen atoms in the side chains at the 1-position and the 4-position does not exceed 4 and with the further proviso that $R_1$ and $R_2$ are not both hydrogen or alkyl; M is selected from the group platinum, copper, iron, zirconium, cobalt, chromium and zinc; X is sulfate, chloride, or nitrate the tautomers thereof; and the pharmacologically acceptable acid-addition salts thereof.

3. The compound according to claim 1 1,4-bis[2-(2-hydroxyethylamino)-ethylamino]-5,8-dihydroxyanthraquinone, tetrachloride, bis(dicyclopentadienyl zirconium chelate).

4. The compound according to claim 1 1,4-bis[2-(2-hydroxyethylamino)ethylamino]-5,8-dihydroxyanthraquinone, tetrachloride, bis(chromium chloride chelate).

5. The compound according to claim 1 1,4-bis[2-(2-hydroxyethylamino)ethylamino]-5,8-dihydroxyanthraquinone, dinitrate, bis(cobalt nitrate chelate).

6. The compound according to claim 1 1,4-bis[2-(2-hydroxyethylamino]-5,8-dihydroxyanthraquinone, dichloride, bis(platinum chloride chelate).

7. The compound according to claim 1 1,4-bis[2-(2-hydroxyethylamino)ethylamino]-5,8-dihydroxyanthraquinone, dichloride, bis(cuprous chloride chelate).

8. The compound according to claim 1 1,4-bis[2-(2-hydroxyethylamino)ethylamino]-5,8-dihydroxyanthraquinone, dichloride, bis(ferrous chloride chelate).

9. The compound according to claim 1 1,4-bis[2-(2-hydroxyethylamino)ethylamino]-5,8-dihydroxyanthraquinone, trisulfate, tris(zinc chelate).

* * * * *